(12) United States Patent
Gan et al.

(10) Patent No.: US 8,956,654 B2
(45) Date of Patent: Feb. 17, 2015

(54) SUSTAINED RELEASE DOSAGE FORM

(75) Inventors: Yong Gan, Shanghai (CN); Chunliu Zhu, Shanghai (CN); Sophie Zhai, Shanghai (CN); Robert I. Schmitt, Annandale, NJ (US); Ka Chun A. Chan, Kowloon (HK)

(73) Assignee: Dow Global Technologies LLC, Midland, MI (US)

(*) Notice: Subject to any disclaimer, the term of this patent is extended or adjusted under 35 U.S.C. 154(b) by 83 days.

(21) Appl. No.: 13/254,115

(22) PCT Filed: Jun. 2, 2009

(86) PCT No.: PCT/CN2009/072099
§ 371 (c)(1),
(2), (4) Date: Nov. 8, 2011

(87) PCT Pub. No.: WO2010/139111
PCT Pub. Date: Dec. 9, 2010

(65) Prior Publication Data
US 2012/0045485 A1    Feb. 23, 2012

(51) Int. Cl.
A61K 9/24 (2006.01)
A61K 9/32 (2006.01)
A61K 9/00 (2006.01)
A61K 31/00 (2006.01)

(52) U.S. Cl.
CPC ............... *A61K 9/0004* (2013.01); *A61K 31/00* (2013.01)
USPC .......................................... 424/473; 424/482

(58) Field of Classification Search
None
See application file for complete search history.

(56) References Cited

U.S. PATENT DOCUMENTS

| | | |
|---|---|---|
| 3,845,770 A | 11/1974 | Theeuwes et al. |
| 3,916,899 A | 11/1975 | Theeuwes et al. |
| 4,034,758 A | 7/1977 | Theeuwes |
| 4,077,407 A | 3/1978 | Theeuwes et al. |
| 4,327,725 A | 5/1982 | Cortese et al. |
| 4,572,909 A | 2/1986 | Campbell et al. |
| 4,612,008 A | 9/1986 | Wong et al. |
| 4,783,337 A | 11/1988 | Wong et al. |
| 5,021,053 A | 6/1991 | Barclay et al. |
| 6,136,347 A | 10/2000 | Pollinger et al. |
| 6,485,748 B1 | 11/2002 | Chen et al. |
| 2008/0038345 A1* | 2/2008 | Oberegger et al. ............ 424/468 |
| 2008/0213381 A1* | 9/2008 | Dharmadhikari et al. .... 424/497 |
| 2009/0004281 A1 | 1/2009 | Nghiem et al. |

FOREIGN PATENT DOCUMENTS

| | | |
|---|---|---|
| CN | 1371680 A | 10/2002 |
| EP | 089167 A2 | 3/1983 |
| EP | 0347024 A2 | 12/1989 |
| EP | 2085078 A1 | 5/2009 |
| WO | 02/062299 A2 | 8/2002 |
| WO | 2006/046114 A2 | 5/2006 |
| WO | 2006/123364 A2 | 11/2006 |
| WO | 2009122431 | 10/2009 |

OTHER PUBLICATIONS

Adalat® OROS Product Information, Bayer Australia Limited, Dec. 15, 2011.
Verma R.K. et al., Formulation aspects in the development of osmotically controlled oral drug delivery systems, Journal of controlled release, 2002, vol. 79, p. 7-27.
Lecomte F. et al., pH-Sensitive Polymer Blends used as Coating Materials to Control Drug Release from Spherical Beads: Importance of the Type of Core, Biomacromolecules, 2005, vol. 6, p. 2074-2083.

* cited by examiner

*Primary Examiner* — H. Sarah Park

(57) ABSTRACT

An osmotic dosage form which comprising:
(a) a core comprising a biologically active ingredient;
(b) a semi-permeable membrane covering said core; and
(c) at least one passageway through the semi-permeable membrane,
wherein the semi-permeable membrane comprises ethyl cellulose, an acrylic or methacrylic polymer and a water-soluble plasticizer with the proviso that the semi-permeable membrane comprises no or not more than 15 weight percent of a water-soluble material excluding any water-soluble plasticizer, based on the total dry weight of the semi-permeable membrane.

6 Claims, 1 Drawing Sheet

SUSTAINED RELEASE DOSAGE FORM

CROSS REFERENCE TO RELATED APPLICATIONS

This application is a 35 USC §371 national phase filing of PCT/CN2009/072099.

FIELD OF THE INVENTION

The present invention relates to osmotic dosage forms which comprise a core comprising a biologically active ingredient, a semi-permeable membrane covering said core; and at least one passageway through the semi-permeable membrane.

BACKGROUND OF THE INVENTION

Osmotic dosage forms are known from U.S. Pat. Nos. 3,845,770; 3,916,899; 4,034,758; 4,077,407; 4,327,725; and 4,783,337. The development of osmotic dosage forms was pioneered by Alza with the development of OROS™, an elementary oral osmotic system. Osmotic dosage forms work on the principle of osmosis and deliver drugs in a near zero order profile. The osmotic dosage forms comprise a core comprising a biologically active ingredient and a semi-permeable membrane covering said core. The semi-permeable membrane, often also called semi-permeable wall, is permeable to the passage of aqueous external fluid, such as gastric or intestinal fluid, and allows the external fluid to permeate the membrane and optionally dissolve the biologically active ingredient. The membrane is substantially impermeable to the passage of the active ingredient in solution or dispersion with the external fluid. An osmotic passageway is provided through the wall to deliver the solution or dispersion of the active ingredient in the external fluid to the environment instead of delivery via diffusion through the membrane. The osmotic dosage forms allow an extended release of an active ingredient. If the osmotic dosage form comprises an active ingredient which is insoluble in the external fluid, the osmotic dosage form often comprises a polymeric swelling agent which expands upon contact with the external fluid and pushes the active ingredient through the passageway. WO 2006/046114 discloses osmotic dosage forms which essentially consist of a core comprising a drug layer and a push layer, a semi-permeable membrane surrounding the core and at least one passageway in the semi-permeable membrane.

The above-mentioned patent publications disclose that materials useful in forming the semi-permeable membrane are cellulose esters, cellulose diesters, cellulose triesters, cellulose ethers, cellulose ester-ethers, cellulose acetate, cellulose diacetate, cellulose triacetate, cellulose acetate proprionate, and cellulose acetate butyrate.

The Chinese Patent publication CN1923184-A discloses osmotic release tablet formulations of venlafaxine hydrochloride, a water soluble drug. The control-release cluster aperture coupled with osmotic pump tablet is composed of a flake core and coating film The coating comprises one or more of film-forming polymers selected from cellulose acetate, ethyl cellulose, hydroxypropyl methylcellulose, and/or polyacrylic resin and further comprises 20 to 45 wt. % of a pore-forming agent, such as sugar, sodium chloride, sorbitol, polyethylene glycol or hydroxypropyl cellulose, based on the weight of the coating. The coating may also comprise a plasticizing agent, such as triethyl citrate, dibutyl sebacate, phthalate ester, and/or polyethylene glycol 4000. Unfortunately, this coating does not have sufficient film strength and may be broken by polymeric swelling agents which are typically included in osmotic release tablets.

The most preferred and well-known semi-permeable membrane material is cellulose acetate. Many commercially used osmotic dosage forms, such as the OROS® Push-Pull™ system developed at ALZA, comprise cellulose acetate as film-forming material for the semi-permeable membrane. In the process for producing the osmotic dosage form a shaped core comprising a biologically active ingredient is typically coated with a starting material for the semi-permeable membrane dissolved in an organic solvent. When the osmotic dosage form comprises cellulose acetate as film-forming material for the semi-permeable membrane, there is a significant lag-time between the intake of the osmotic dosage form by an individual such as a human being, and the onset of the release of the biologically active ingredient. Moreover, cellulose acetate has to be dissolved in acetone for preparing the semi-permeable membrane, which is undesirable for safety reasons.

Several attempts have been made by the skilled artisans to overcome this lag-time. The most common approach is to coat the osmotic dosage form with an external immediate release coating layer that comprises the biologically active ingredient. Unfortunately, such additional external immediate release coating layer adds to the complexity and costs of osmotic dosage forms. Moreover, an external coating layer comprising the biologically active ingredient is often undesirable for product safety reasons.

Accordingly, it would be desirable to provide a new osmotic dosage form which does not comprise cellulose acetate as the film-forming material for the semi-permeable membrane. It would be more desirable to provide a new osmotic dosage form which does not have a significant lag-time between the intake of the osmotic dosage form and the onset of the release of the biologically active ingredient which is experienced with osmotic dosage forms comprising cellulose acetate as the film-forming material for the semi-permeable membrane. It would be particularly desirable to provide a new osmotic dosage form which provides a substantially zero order profile during a time period of 2 to 12 hours after the contact with an aqueous liquid has started. It would also be particularly desirable to provide a new osmotic dosage form that has sufficient film strength such that it is not broken by polymeric swelling agents which are typically included in osmotic dosage forms.

SUMMARY OF THE INVENTION

One aspect of the present invention is an osmotic dosage form (101, 201, 301) comprising:
(a) a core (102, 202, 302) comprising a biologically active ingredient (204);
(b) a semi-permeable membrane (105, 205, 305) covering said core; and
(c) at least one passageway (106, 206, 306) through the semi-permeable membrane,
wherein the semi-permeable membrane comprises ethyl cellulose, an acrylic or methacrylic polymer and a water-soluble plasticizer, with the proviso that the semi-permeable membrane comprises no or not more than 15 weight percent of a water-soluble material excluding any water-soluble plasticizer, based on the total dry weight of the semi-permeable membrane.

Another aspect of the present invention is a process for preparing the above-mentioned osmotic dosage form which comprises the steps of
I) forming a core from the biologically active ingredient and optional ingredients;

II) coating the core with a membrane composition comprising ethyl cellulose, an acrylic or methacrylic polymer, a water-soluble plasticizer and optional ingredients to provide a semi-permeable membrane;
III) creating at least one passageway in the semi-permeable membrane; and optionally
IV) applying a finishing layer to the osmotic dosage form.

DETAILED DESCRIPTION OF THE INVENTION

Figure 1:
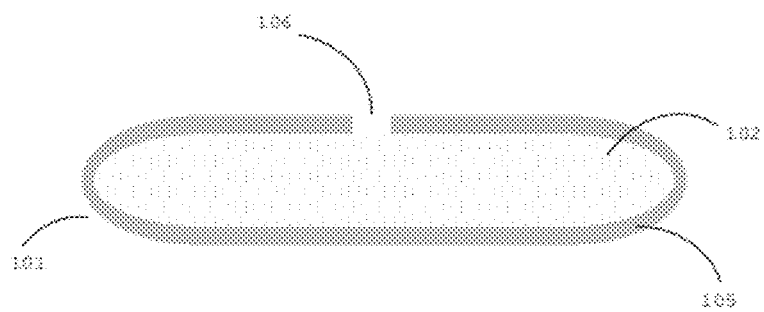
FIGS. 1-3 illustrate three different embodiments of the osmotic dosage form of the present invention.

The main aspect of the present invention relates to the semi-permeable membrane (b) of the osmotic dosage form. The semi-permeable membrane (b) is permeable to an external aqueous fluid, such as gastric or intestinal fluid, while essentially impermeable to a selected product in the core (a), such as the biologically active ingredient. The semi-permeable membrane (b) generally maintains its physical and chemical integrity during the time the biologically active ingredient is released.

It has surprisingly been found that semi-permeable membranes comprising ethyl cellulose, an acrylic or methacrylic polymer and a water-soluble plasticizer are suitable substitutes for semi-permeable membranes comprising cellulose acetate as the film-forming material in osmotic dosage forms, provided that the semi-permeable membrane comprises no or not more than 15 weight percent of a water-soluble material excluding any water-soluble plasticizer, based on the total dry weight of the semi-permeable membrane. The semi-permeable membranes of the present invention do not comprise more than 15 weight percent of a water-soluble material, in addition to the water-soluble plasticizer.

At least in the preferred embodiments of the osmotic dosage form of the present invention, the accumulated drug release in percent between 2 and 12 hours meets the formula for zero order release:
Y=100k(t−Tlag) after fitting test. Tlag means the lagging time, which is 2 hours. Y is the accumulated drug release in percent and k is a constant. After linear fitting, $R^2$ is >0.9, preferably >0.95.

The term "the total dry weight" used in connection with the osmotic dosage form, the core, the semi-permeable membrane, the drug layer, and the push layer means the total weight of all ingredients except water or liquid organic solvents, such as alcohols.

The term "water-soluble" as used herein applies to plasticizers, polymers and other materials and encompasses the terms "very soluble", "freely soluble" and "soluble" as defined in the US Pharmacopeia listed below. The solubilities are measured at 25° C.

| Descriptive Term | Volume Parts of Solvent Required for 1 Part of Solute[1] |
| --- | --- |
| Very soluble | Less than 1 |
| Freely soluble | From 1 to 10 |
| Soluble | From 10 to 30 |
| Sparingly soluble | From 30 to 100 |
| Slightly soluble | From 100 to 1000 |
| Very slightly soluble | From 1000 to 10,000 |
| Practically insoluble, or insoluble | 10,000 and over |

[1]For solutes that are liquid at 25° C., 1 Part of Solute means a Volume Part; for solutes that are solid at 25° C., 1 Part of Solute means a Weight Part The semi-permeable membrane comprises ethyl cellulose, preferably in such an amount that ethyl cellulose is the film-forming polymer of the semi-permeable membrane. The use of ethyl cellulose is very advantageous since it can be dissolved for providing a coating composition in the absence of acetone. Moreover, it has been found that the osmotic dosage form of the present invention can be designed in such a manner that it does not have a significant lag-time between the intake of the osmotic dosage forms and the onset of the release biologically active ingredient. Moreover, it has been found that at least the preferred embodiments of the osmotic dosage form of the present invention provide a substantially zero order release profile for biologically active ingredients during a time period of 2 to 12 hours after the contact with an aqueous liquid has started.

The ethylcellulose preferably has an ethoxyl content of from 40 to 55 percent, more preferably from 43 to 53 percent, most preferably from 45 to 52 percent. The percent ethoxyl substitution is based on the weight of the substituted product and determined according to a Zeisel gas chromatographic technique as described in ASTM D4794-94 (2003). These ethoxyl contents correspond to an ethyl DS of from 1.9 to 3.0, preferably from 2.1 to 2.9, more preferably from 2.3 to 2.8. The molecular weight of the ethylcellulose is expressed as the viscosity of a 5 weight percent solution of the ethylcellulose measured at 25° C. in a mixture of 80 volume percent toluene and 20 volume percent ethanol. The ethylcellulose concentration is based on the total weight of toluene, ethanol and ethylcellulose. The viscosity is measured using Ubbelohde tubes as outlined in ASTM D914-00 and as further described in ASTM D446-04, which is referenced in ASTM D914-00. The ethylcellulose preferably has a viscosity of from 2 mPa·s, more preferably from 5 Pa·s; most preferably from 10 mPa·s, to 400 mPa·s, preferably to 100 mPa·s, more preferably to 50 mPa·s. Preferably the amount of ethyl cellulose is from about 10 to about 90 percent, more preferably from about 20 to about 80 percent, and most preferably from about 30 to about 70 percent, based on the total dry weight of the semi-permeable membrane.

The semi-permeable membrane further comprises an acrylic or methacrylic polymer, such as a homopolymer or copolymer comprising polymerized units of acrylic acid, methacrylic acid, an acrylic acid ester, a methacrylic acid ester or a combination thereof, preferably a homopolymer or copolymer comprising polymerized units of acrylic acid, methacrylic acid, a $C_{1-4}$-alkyl ester of acrylic acid or methacrylic acid, an amino $C_{1-4}$-alkyl ester of acrylic acid or methacrylic acid or a combination thereof, such as polymerized units of methacrylic acid, acrylic acid ethyl ester (ethyl acrylate), acrylic acid methyl ester (methyl acrylate), methacrylic acid methyl ester (methyl methacrylate), methacrylic acid butyl ester (butyl methacrylate), methacrylic acid dimethylaminoethyl ester (dimethylaminoethyl methacrylate), acrylic acid dimethylaminoethyl ester (dimethylaminoethyl acrylate), methacrylic acid trimethylammoniumethyl ester, acrylic acid trimethylammoniumethyl ester or a combination thereof, including the Eudragit family of polymers available from Evonik Industries. The acrylic or methacrylic polymer is preferably a homo- or copolymer of the above-mentioned monomers. The acrylic or methacrylic polymers are typically water-insoluble polymers. The acrylic and methacrylic polymers of the Eudragit family are well known in the art and include a number of different polymers, ranging from Eudragit L100-55 (the spray dried form of Eudragit L30D), Eudragit L30D, Eudragit L100, Eudragit S100, Eudragit 4135F, Eudragit E100, Eudragit EPO (powder form of E100), Eudragit RL30D, Eudragit RL PO, Eudragit RL 100, Eudragit RS 30D, Eudragit RS PO, Eudragit RS 100, Eudragit NE 30 D, and Eudragit NE 40 D. Preferably the amount of the acrylic or methacrylic polymer is from about 2 to about 60 percent, more preferably from about 5 to about 40 percent, and most preferably from about 10 to about 30 percent, based on the total dry weight of the semi-permeable membrane.

The weight ratio between the ethyl cellulose and the acrylic or methacrylic polymer in the semi-permeable membrane preferably is from about 0.1-15:1, more preferably from about 0.5-10:1, most preferably from about 1-5:1.

The semi-permeable membrane further comprises a water-soluble plasticizer. Typical water-soluble plasticizers are monomeric compounds or oligomeric compounds having a weight average molecular weight of up to 10,000, preferably triethyl citrate, triacetin, polyethylene glycol, particularly polyethylene glycol with a weight average molecular weight of 2000 to 6000, such as PEG 4000, a polyoxyethylene sorbitan monooleate, commercially available under the trademark Tween, such as Tween 20 or Tween 80, and, most preferably, glycerol. Preferably the amount of the water-soluble plasticizer is from about 2 to about 70 percent, more preferably from about 5 to about 50 percent, and most preferably from about 10 to about 40 percent, based on the total dry weight of the semi-permeable membrane.

The weight ratio between the ethyl cellulose and the water-soluble plasticizer in the semi-permeable membrane preferably is from about 0.1-20:1, more preferably from about 0.5-10:1, most preferably from about 0.9-3.4:1.

Generally the total amount of ethyl cellulose, the acrylic or methacrylic polymer, and the water-soluble plasticizer is from about 85 to 100 percent, preferably from about 90 to 100 percent, more preferably from about 95 to 100 percent, most preferably from about 98 to 100 percent, based on the total dry weight of the semi-permeable membrane.

The semi-permeable membrane does not comprises more than about 15 percent, preferably not more than about 10 percent, more preferably not more than about 5 percent, most preferably not more than about 2 percent of a water-soluble material other than the water-soluble plasticizer, based on the total dry weight of the semi-permeable membrane. Particularly, excluding the water-soluble plasticizer, the semi-permeable membrane comprises no or not more than about 15 percent, preferably not more than about 10 percent, more preferably not more than about 5 percent, most preferably not more than about 2 percent of an water-soluble material that is known as a pore-forming agent. Known examples of pore-forming agents are sodium chloride, potassium chloride, sucrose, sorbitol, mannitol, or hydroxy propyl cellulose. If the semi-permeable membrane comprises more than 15 percent of a pore-forming agent in addition to the water-soluble plasticizer, an unduly high amount of the biologically active ingredient will be released through the membrane which is undesirable for the osmotic dosage form of the present invention.

The semi-permeable membrane may comprise further optional additives, such as water-insoluble plasticizers. Examples of water-insoluble plasticizers include adipates, azelates, enzoates, citrates, stearates, isoebucates, sebacates, such as tri-n-butyl citrate, acetyl tri-n-butyl citrate, and citric acid esters, The preferred water-insoluble plasticizers are acetylated monoglyceride, grape seed oil, olive oil, sesame oil, acetyltributyl citrate, acetyltriethyl citrate, tributyl citrate, diethyl oxalate, diethyl malate, diethyl fumarate, dibutyl succinate, diethyl malonate, diethyl phthalate, dibutyl phthalate, dioctyl phthalate, dibutyl sebacate and glycerol tributyrate. The most preferred water-insoluble plasticizers are acetyltriethyl citrate, acetyltributyl citrate, tributyl citrate, diethyl phthalate, dibutyl phthalate and dibutyl sebacate.

If the semi-permeable membrane comprises one or more optional additives, their total amount is generally up to about 15 percent, preferably up to about 10 percent, more preferably up to about 5 percent, based on the total dry weight of the semi-permeable membrane.

Preferably, the semi-permeable membrane (b) around the core (a) is from about 10 to about 45 percent, preferably from about 15 to 35 percent, most preferably about 20 to 30 percent, based on the weight of the core (a).

The core (a) of the osmotic dosage form of the present invention can comprise a wide range of biologically active ingredients, such as vitamins, herbals and mineral supplements and drugs. The biologically active ingredient includes hydrophobic, hydrophilic and amphiphilic compounds. Drugs may be in the form of pharmaceutically acceptable salts, solvates, enantiomers, esters, and mixtures thereof. Suitable examples include drugs belonging to the class of central nervous system stimulants, opioids, antidiabetics, antineoplastic agents, antihypertensives, hypnotics, barbiturates, psychostimulants, cannabinoids, catecholamines, cardiovascular agents, platelet aggregation inhibitors, analgesics, antimicrobials, diuretics, and spasmolytics although other classes may be used as desired. Specific examples include methylphenidate, amphetamines, glipizide, doxazosin, isradipine, nifedipine, nisoldipine, bendroflumethazide, chlorpropamide, hydrocortisone, ibuprofen, diclofenac, oxycodone, isosorbide mononitrate, tamsulosin hydrochloride, methylphenidate hydrochloride, verapamil hydrochloride, itopride hydrochloride, salbutamol aerosol, diltiazem hydrochloride, pseudoephedrine hydrochloride, oxybutynin hydrochloride, phenylpropanolamine hydrochloride, felodipine, haloperidol, desvenlafaxin, carbamazepine, isradipine, doxazosin mesylate, metformin and carvedilol. Other useful drugs that are very soluble or poorly soluble in water are disclosed in U.S. Pat. No. 5,021,053, column 10, lines 26-68 and column 11, lines 1-50. The drug preferably constitutes from about 1 to about 80 percent, more preferably from about 4 to about 50 percent, of the total dry weight of the core (a) (not including coating weight).

The core can consist of one layer comprising the biologically active material, such as illustrated in FIG. 1. A core consisting of one layer is described further below.

Figure 2:
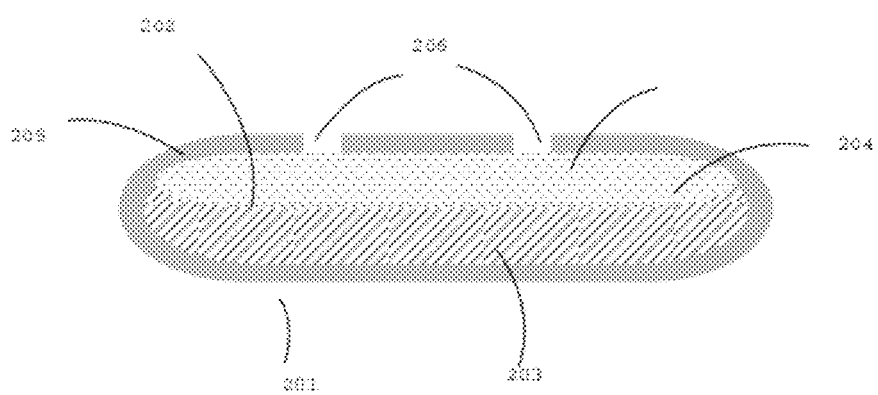
Figure 3:
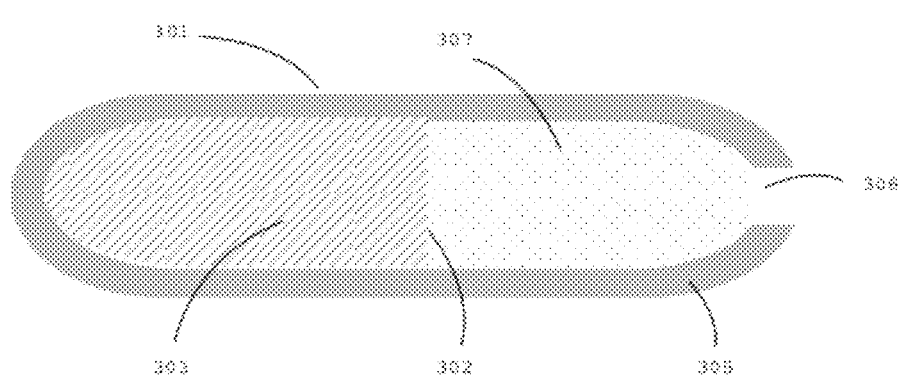

Alternatively the core can consist of two layers, such as illustrated in FIGS. 2 and 3, or even more layers, typically three layers (not illustrated). In such embodiment of the present invention the core (a) comprises (i) a first layer comprising the biologically active ingredient, commonly called "drug layer", and (ii) a second layer comprising a polymeric swelling agent. The second layer is commonly called "push layer" since the polymeric swelling agent expands upon contact with the external fluid and pushes the active ingredient through the passageway. Preferably the drug layer constitutes from about 5 to about 95 percent, more preferably from about 50 to about 80 percent, of the total dry weight of the core (a). The push layer preferably constitutes from about 5 to about 95 percent, more preferably from about 20 to about 50 percent, of the total dry weight of the core (a).

The drug layer preferably comprises about 1 to about 80 weight percent, more preferably from about 4 to about 50 weight percent of one or more biologically active materials as described above, based on the dry weight of the drug layer.

The drug layer preferably comprises a non-cross-linked or lightly cross-linked hydrophilic polymer, which acts as a polymeric suspending agent for the biologically active material after the external fluid has permeated the membrane.

Preferred polymeric suspending agents include poly(hydroxy alkyl methacrylate) having a molecular weight of from 30,000 to 1,000,000; poly(vinylpyrrolidone) having a molecular weight of from 10,000 to 360,000; anionic and cationic hydrogels; poly(vinyl alcohol) having a low acetate residual, optionally cross-linked with glyoxal, formaldehyde, or glutaraldehyde and having a degree of polymerization from 200 to 30,000; methyl cellulose; carboxymethyl cellulose; or water swellable polymers of N-vinyl lactams. Preferred polymers are those that form hydrogels such as Carbopol™ acidic carboxy polymers having a molecular weight of 450,000 to 1,000,000; Cyanamer™ polyacrylamides; cross-linked water swellable indene-maleic anhydride polymers, Goodrite™ polyacrylic acid having a molecular weight of 80,000 to 200,000; Polyox™ polyethylene oxide polymers having molecular weight of from about 100,000 to less than 1,000,000, more preferably of from about 100,000 to about 500,000, most preferably of from about 100,000 to about 300,000; hydroxypropyl methylcellulose or starch graft copolymers. Representative polymers that form hydrogels are known to the prior art in U.S. Pat. Nos. 3,865,108 issued to Hartop; 4,002,173 issued to Manning; 4,207,893 issued to Michaels; and in Handbook of Common Polymers, by Scott and Roff, published by the Chemical Rubber Company, Cleveland, Ohio. The most preferred hydrophilic suspending agents are ethylene oxide polymers, more preferably those commercially available from The Dow Chemical company under the trademark Polyox™ WSR. It is available in various grades depending on its molecular weight MW. The weight average molecular weight MW of polyethylene oxide may generally vary from about 100,000 to less than 1,000,000, more preferably of from about 100,000 to about 500,000, most preferably of from about 100,000 to about 300,000. Examples of preferred grades of polyethylene oxide include POLYOX™ WSR N-10 (MW about 100,000), WSR N-80 (MW about 200,000), and WSR N-750 (MW about 300,000). The polymeric suspending agent preferably constitutes from 0 to about 97 percent, more preferably from about 15 to about 90 percent, most preferably from about 50 to about 90 percent of the total dry weight of the drug layer in the core (a).

The drug layer may further comprise one or more pharmaceutically acceptable inert excipients. The term "pharmaceutically acceptable inert excipients" as used herein includes all excipients used in the art of manufacturing osmotic controlled dosage forms and described in the literature. Specific examples include binding agents, osmotic agents, lubricants/glidants, diluents, surfactants, pH modifiers, stabilizers and pigments/coloring agents.

The drug layer preferably comprises a binding agent which is different from the hydrophilic polymer acting as a polymeric suspending agent for the biologically active material. Preferred examples of binding agents include methyl cellulose, hydroxypropyl cellulose, hydroxyethyl cellulose, hydroxypropyl methylcellulose, carboxymethyl cellulose, preferably in the form of a physiologically acceptable salt, polyvinylpyrrolidone, gelatin, gum arabic, polyvinyl alcohol, pullulan, pregelatinized starch, agar, tragacanth, sodium alginate or propylene glycol. The binding agent is preferably water soluble and physiologically acceptable. The binding agent preferably constitutes from 0 to about 30 percent, more preferably from 0 to about 10 percent of the total dry weight of the drug layer in the core (a).

Furthermore, the drug layer preferably comprises an osmotic agent. The term "osmotic agent" as used herein includes all pharmaceutically acceptable inert water soluble compounds suitable for inducing osmosis, referred to in the Pharmacoepias, or in "Hager" as well as in Remington's Pharmaceutical sciences. Examples of compounds suitable as osmotic agents include water soluble salts of inorganic acids such as magnesium chloride or magnesium sulfate, lithium chloride, sodium chloride, potassium chloride, lithium hydrogen phosphate, sodium hydrogen phosphate, potassium hydrogen phosphate, lithium dihydrogen phosphate, sodium dihydrogen phosphate, and potassium dihydrogen phosphate; water soluble salts of organic acids such as sodium acetate, potassium acetate, magnesium succinate, sodium benzoate, sodium citrate, and sodium ascorbate; non ionic organic compounds with high water solubility, e.g., carbohydrates such as mannitol, sorbitol, arabinose, ribose, xylose, glucose, fructose, mannose, galactose, sucrose, maltose, lactose, and raffinose; water-soluble amino acids such as glycine, leucine, alanine, or methionine; urea and urea derivatives. The osmotic agent preferably constitutes from 0 to about 30 percent, more preferably from 0 to about 20 percent, most preferably from 0 to about 10 percent of the total dry weight of the drug layer in the core (a).

Advantageously the drug layer additionally comprises a lubricant, also designated as "glidant". Specific examples of lubricants include colloidal silicon dioxide, stearic acid, magnesium stearate, calcium stearate, talc, hydrogenated castor oil, sucrose esters of fatty acid, microcrystalline wax, yellow beeswax or white beeswax. Their amount is preferably from 0 to about 2 percent, more preferably from 0 to about 1 percent, based on the total weight of the drug layer in the core (a).

The drug layer may additionally comprise a pH modifier. The pH modifiers are substances which help in maintaining the pH of the local environment surrounding the drug at a value favorable for dissolution or suspension of drug. Specific examples of pH modifiers include dibasic sodium phosphate, sodium ascorbate, meglumine, sodium citrate, trimethanolamine, sodium hydroxide, potassium hydroxide, calcium hydroxide, magnesium oxide, magnesium hydroxide, ammonia, tertiary sodium phosphate, diethanolamine, ethylenediamine or L-lysine.

Specific examples of diluents include calcium carbonate, dibasic and tribasic calcium phosphate, calcium sulfate, microcrystalline or powdered cellulose, dextrates, dextrins, dextrose excipients, fructose, kaolin, lactitol, lactose, mannitol, sorbitol, starch, pregelatinized starch, sucrose, or sugar.

Preferred pigments or coloring agents include any FDA approved colors for oral use, such as iron oxide. Their amount is preferably from 0 to about 3 percent, more preferably from 0 to about 2 percent, based on the total weight of the drug layer in the core (a).

Preferred stabilizers include antioxidants or buffers.

The push layer typically comprises a polymeric swelling agent. The polymeric swelling agent preferably constitutes from about 5 to about 70 percent, more preferably from about 15 to about 60 percent, most preferably from about 25 to about 60 percent, based on the total dry weight of the push layer. The polymeric swelling agent is typically a hydrophilic polymer that is designed to swell or expand in contact with water or an aqueous biological fluid. The swelling agent exhibits the ability to retain a significant portion of the imbibed water within the polymer structure. Typically the polymeric swelling agent swells or expands to a very high degree, usually exhibiting a 2 to 50 fold volume increase. Above-mentioned hydrophilic polymers are useful as polymeric swelling agent, provided they have the desired swelling properties. Usually the polymeric swelling agent has a higher molecular weight than the hydrophilic polymer that is used in the drug layer as a suspending agent. The most preferred polymeric swelling agents are ethylene oxide polymers, more preferably Polyox™ polyethylene oxide or hydroxypropyl methylcellulose. The weight average molecular weight of polyethylene oxide may generally vary from about 1,000,000 to about 7,000,000 and more particularly from about 4,000,000 to about 7,000,000. Particularly preferred are POLYOX WSR-N750, POLYOX™ WSR Coagulant, POLYOX™ WSR-301, and/or WSR-303.

The push layer may further comprise one or more pharmaceutically acceptable inert excipients, such as a binding agent, an osmotic agent, lubricant, pH modifier, diluent, pigment or stabilizer. Preferred excipients are those described above for the drug layer. The push layer preferably comprises a different pigment than the drug layer.

The binding agent preferably constitutes from 0 to about 20 percent, more preferably from about 1 to about 10 percent of the total dry weight of the push layer in the core (a).

The osmotic agent preferably constitutes from 0 to about 60 percent, more preferably from about 15 to about 50 percent of the total dry weight of the push layer in the core (a).

Alternatively, the core can consist of one layer comprising the biologically active material, such as illustrated in FIG. 1. This layer advantageously comprises a biologically active material of the type and amount described for the drug layer and a polymeric swelling agent of the type and amount described for the push layer above. The push layer may further comprise one or more pharmaceutically acceptable inert excipients, such as a binding agent, an osmotic agent, lubricant, pH modifier, diluent, or stabilizer of the types and amounts described for the drug layer. Typically no suspending agent is included in a one-layered core.

As used herein the term passageway includes an aperture, orifice, bore, hole, weaken area or an erodible element such as a gelatin plug that erodes to form an osmotic passageway for the release of the biologically active ingredient from the dosage form. A detailed description of the passageway can be found in U.S. Pat. Nos. 3,845,770; 3,916,899; 4,034,758; 4,077,407; 4,783,337 and 5,071,607. Preferably drilling, such as mechanical drilling or, more preferably, laser drilling through the semi-permeable membrane is used to form the passageway.

More preferred are osmotic dosage forms wherein the core
(a) comprises
(ai) a drug layer comprising a biologically active ingredient, one or more ethylene oxide polymers, optionally one or more binding agents, optionally one or more osmotic agents, optionally a pigment and optionally a lubricant;
(aii) a push layer comprising one or more ethylene oxide polymers, optionally one or more binding agents, optionally one or more osmotic agents, optionally a pigment and optionally a lubricant; and
the semi-permeable membrane (b) comprises ethyl cellulose, an acrylic or methacrylic polymer, and a water-soluble plasticizer selected from the group consisting of triethyl citrate, triacetin, polyethylene glycol, and glycerol, with the proviso that the semi-permeable membrane comprises no or not more than 10 weight percent of a water-soluble material excluding any water-soluble plasticizer, based on the total dry weight of the semi-permeable membrane.

Most preferred are osmotic dosage forms wherein
the core (a) comprises
(ai) a drug layer comprising, based on the total weight of the drug layer, from about 1 to about 80 weight percent, more preferably from about 4 to about 50 weight percent of the biologically active ingredient, from about 15 to about 90 weight percent, most preferably from about 50 to about 90 weight percent of one or more ethylene oxide polymers, from 0 to about 10 weight percent of one or more binding agents selected from the group consisting of methyl cellulose, hydroxypropyl cellulose, hydroxyethyl cellulose, hydroxypropyl methylcellulose, carboxymethyl cellulose, and polyvinyl pyrrolidone, from 0 to about 30 percent, more preferably from 0 to about 20 percent, most preferably from 0 to about 10 percent by weight of an osmotic agent, from 0 to about 3 percent, more preferably from 0 to about 2 percent by weight of a pigment and from 0 to about 2 percent, more preferably from 0 to about 1 percent by weight of a lubricant;
(aii) a push layer comprising, based on the total weight of the push layer, from about 5 to about 70 percent, more preferably from about 15 to about 60 percent, most preferably from about 25 to about 60 percent of one or more ethylene oxide polymers, from 0 to about 20 percent, more preferably from about 1 to about 10 percent by weight of one or more binding agents selected from the group consisting of methyl cellulose, hydroxypropyl cellulose, hydroxyethyl cellulose, hydroxypropyl methylcellulose, carboxymethyl cellulose, and polyvinyl pyrrolidone, from 0 to about 60 percent, more preferably from about 15 to about 50 percent by weight of one or more osmotic agents, from 0 to about 2 percent by weight of a pigment and from 0 to about 2 percent, more preferably from 0 to about 1 percent by weight of a lubricant; and
the semi-permeable membrane (b) comprises, based on the total dry weight of the semi-permeable membrane (b), from about 10 to about 90 percent, more preferably from about 20 to about 80 percent, and most preferably from about 30 to about 70 percent of ethyl cellulose, from about 2 to about 60 percent, more preferably from about 5 to about 40 percent, and most preferably from about 10 to about 30 percent of an acrylic or methacrylic polymer and from about 2 to about 70 percent, more preferably from about 5 to about 50 percent, and most preferably from about 10 to about 40 percent of a water-soluble plasticizer selected from the group consisting of triethyl citrate, triacetin, and glycerol, with the proviso that the semi-permeable membrane comprises no or not more than about 10 percent, more preferably not more than about 5 percent, most preferably not more than about 2 percent by weight of a water-soluble material excluding any water-soluble plasticizer.

The osmotic dosage form of the present invention may additionally comprise a finishing layer on the semi-permeable membrane. The finishing layer is preferably water soluble and may be colored or clear, such as the coatings known under the trademark Opadry and Opadry Clear.

At least in the preferred embodiments of the osmotic dosage form of the present invention, the accumulated drug release in percent meets the formula for zero order release when the time t is between 2 and 12 hours:
$Y=100k(t-Tlag)$ after fitting test. Tlag means the lagging time, which is 2 hours. Y is the accumulated drug release in percent and k is a constant. After linear fitting, the correlation coefficient $R^2$ is >0.9, preferably >0.95.

The osmotic dosage form of the present invention can be manufactured by standard techniques. The manufacturing method comprises the steps of
I) forming a core from the biologically active ingredient and optional ingredients,
II) coating the core with a membrane composition comprising ethyl cellulose, an acrylic or methacrylic polymer, a water-soluble plasticizer and optional ingredients to provide a semi-permeable membrane;
III) creating at least one passageway in the semi-permeable membrane; and optionally IV) applying a finishing layer to the osmotic dosage form.

In a preferred aspect the manufacturing method comprises the steps of

Ia) blending the biologically active ingredient with a polymeric suspending agent and one or more optional ingredients and optionally granulating the blend;

Ib) blending a polymeric swelling agent with one or more additional ingredients and optionally granulating the blend;

Ic) combining the blend or granules of step Ia) to a first layer and the blend or granules of step Ib) to a second layer and combining the two layers to produce a core (a) comprising (i) a first layer comprising the biologically active ingredient, the hydrophilic suspending agent and optional ingredients and (ii) a second layer comprising the polymeric swelling agent and additional ingredients;

II) coating the core (a) with a membrane composition comprising ethyl cellulose, an acrylic or methacrylic polymer, a water-soluble plasticizer and optional ingredients to provide a semi-permeable membrane;

III) creating at least one passageway in the semi-permeable membrane; and optionally IV) applying a finishing layer to the osmotic dosage form.

In steps I), Ia) and Ib) respectively the biologically active ingredient and other ingredients can be blended in a known manner. The blends are optionally granulated, preferably by a known wet granulation technique, for example by using water or an alcohol such as ethanol for wet granulation, followed by drying of the granules where appropriate and an optional sieving step. The optionally granulated blends can be pressed into a preselected shape by a tableting process. If at least one separate drug layer and at least one separate push layer have been prepared, the layers can be combined in the manner illustrated by FIGS. 2 and 3.

The semi-permeable membrane can be applied to the pressed shape by molding, spraying or dipping the pressed shape into a starting material for the semi-permeable membrane or by an air suspension procedure as described in U.S. Pat. No. 2,779,241; J. Am. Pharm. Assoc., Vol. 48, pages 451 to 459, 1979; and ibid, Vol. 49, pages 82 to 84, 1960. Other standard manufacturing procedures are described in Modern Plastics Encyclopedia, Vol. 46, pages 62 to 70, 1969; and in Pharmaceutical Sciences, by Remington, Fourteenth Edition, pages 1626 to 1678, 1970, published by Mack Publishing Company, Easton, Penna. The starting material for the semi-permeable membrane typically comprises one or more solvents besides ethyl cellulose, acrylic or methacrylic polymer and one or more optional additives. The solvents broadly include members selected from the group consisting of aqueous solvents, alcohols, ketones, esters, ethers, aliphatic hydrocarbons, halogenated solvents, cycloaliphatic, aromatics, heterocycyclic solvents, and mixtures thereof. Typical solvents include methanol, ethanol, isopropyl alcohol, butyl alcohol, methyl acetate, ethyl acetate, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclooctane, benzene toluene, naphtha, 1,4-dioxane, tetrahydrofuran, diglyme, water, and mixtures thereof (please delete the listed solvents that are not useful). The most preferred solvents are alcohols, such as ethanol. The use of acetone is not required for dissolving ethyl cellulose, the acrylic or methacrylic polymer and the water-soluble plasticizer.

The preferred embodiments of the invention are described with reference to the drawings.

FIG. 1 illustrates an osmotic dosage form 101 which comprises a core 102, a semi-permeable membrane 105 and one or more passageways 106.

FIG. 2 illustrates a preferred embodiment of a osmotic dosage form 201 comprising a core 202. The core consists of a push layer 203 and a drug layer 207 which comprises a biologically active ingredient 204. The core is covered by a semi-permeable membrane 205. Passageways 206 in the semi-permeable membrane 205 connects the ingredients of the core that are not able to pass through the semi-permeable membrane 205 with the exterior of the osmotic dosage form 201.

FIG. 3 illustrates another preferred embodiment of a osmotic dosage form 301 comprising a core 302. The core consists of a push layer 303 and a drug layer 307 which comprises a biologically active ingredient (not shown). The core is covered by a semi-permeable membrane 305. A passageway 306 in the semi-permeable membrane 305 connects the ingredients of the core that are not able to pass through the semi-permeable membrane 305 with the exterior of the osmotic dosage form 301.

When the osmotic dosage form 101, 202 or 301 is put in an exterior aqueous fluid, such as water, gastric or intestinal fluid, the aqueous fluid, mainly water, enters through the passageway 106, 206, 306 and the semi-permeable membrane 105, 205, 305 into the core 102, 202, 302 and the drug (204 in FIG. 2, indicated by dots) is partially or fully dissolved or suspended in the aqueous fluid (not shown), optionally under the effect of an osmotic agent (not shown). The core 102, preferably the push layer 203, 303, comprises a polymeric swelling agent (not shown) that swells upon absorption of water and pushes the drug in the core 102, preferably in the drug layer 207, 307, through the passageway 106, 206, 306 and thereby provides a sustained or controlled release of the drug.

A particularly preferred embodiment of the present invention is indicated in Table 1.

TABLE 1

| Osmotic Dosage form | Ingredient | Preferred Range (%) | Most preferred Range (%) |
|---|---|---|---|
| Drug layer, weight ranges of ingredients are based on total weight of drug layer | Glipizide or another biologically active ingredient | 1-80 | 4-50 |
| | Polyethylene oxide, preferably having a weight average molecular weight of <1,000,000, more preferably POLYOX ™ WSR N-10, WSR N-80 or WSR N-750 | 0-97 | 15-90 |
| | hydroxypropyl methyl cellulose (binder) | 0-30 | 0-10 |

TABLE 1-continued

| Osmotic Dosage form | Ingredient | Preferred Range (%) | Most preferred Range (%) |
|---|---|---|---|
| | Sodium chloride or another osmotic agent | 0-30 | 0-10 |
| | Iron oxide or another pigment | 0-3 | 0-2 |
| | Magnesium stearate or another lubricant | 0-2 | 0.-1 |
| Push layer, weight ranges of ingredients are based on total weight of push layer | Polyethylene oxide having a weight average molecular weight of 1,000,000 or more, preferably POLYOX WSR Coagulant, WSR-301 or WSR-303 | 5-70 | 15-60 |
| | hydroxypropyl methyl cellulose (binder), preferably having a viscosity of 4-6 mPa · s as a 2 wt. % solution | 0-20 | 1-10 |
| | Sodium chloride or another osmotic agent | 0-60 | 15-50 |
| | Iron oxide or another pigment | 0-3 | 0-2 |
| | Magnesium stearate or another lubricant | 0-2 | 0-1 |
| Semi-permeable membrane, weight ranges are based on total weight of membrane | Ethyl cellulose, preferably having a viscosity of 3-50 mPa · s, more preferably of 18-22 mPas | 10-90 | 30-70 |
| | Eudragit polymer, preferably Eudragit RL 100 | 2-60 | 5-40 |
| | Glycerol | 2-70 | 10-40 |

Drug layer is preferably 5-95 percent, more preferably 50-80 percent of the core
Push layer is preferably 5-95 percent, more preferably 20-50 percent of the core The invention is further illustrated by the following Examples which are not to be construed to limit the scope of the protection. Unless otherwise indicated, all percentages, parts and rations are by weight.

EXAMPLES 1-4 AND COMPARATIVE EXAMPLE B

Osmotic dosage forms are prepared according to the following general procedure. The ingredients and their amounts are listed in Table 2.

Drug Layer

Glipizide, Polyox™ WSR N-80 and $Fe_2O_3$ are blended and screened through a 60 mesh sieve. The blend is wet granulated using 95% ethanol. The granules are screened through a 20 mesh sieve. The granules are dried in an oven at 40° C. for 12 hours and then subjected to grinding. The granules are sieved through an 18 mesh sieve and blended with magnesium stearate.

Push Layer

Polyox™ WSR Coagulant, Polyox™ WSR N-750, Methocel E5 cellulose ether, NaCl and $Fe_3O_4$ are blended and screened through a 60 mesh sieve. Methocel E5 cellulose ether is a Hypromellose 2910 in US pharmacopeia and has a methoxyl substitution of about 29 percent, a hydroxypropoxyl substitution of about 10 percent and a viscosity of 4-6 mPa·s, measured as a 2 weight percent aqueous solution using an Ubbelohde viscometer at 20° C. The blend is wet granulated using 97.5% ethanol. The granules are screened through a 20 mesh sieve. The granules are dried in an oven at 40° C. for 12 hours and then subjected to grinding. The granules are sieved through an 18 mesh sieve and blended with magnesium stearate.

Semipermeable Membrane of Examples 1 to 4

30 g of ETHOCEL Standard 20 ethyl cellulose are dissolved in 400 mL of 95% ethanol. ETHOCEL Standard 20 ethyl cellulose has a solution viscosity of 18-22 cP (mPa·S), measured as a 5 wt. % solution at 25° C. in an Ubbelohde viscosimeter. The solvent is 80% toluene and 20% ethanol. The ethoxyl content is 48.0-49.5 percent. ETHOCEL Standard 20 ethyl cellulose is commercially available from The Dow Chemical Company. 7.5 g of EUDRAGIT™ RL 100 are dissolved in 100 mL of 95% ethanol. EUDRAGIT™ RL 100 is as copolymer of acrylic and methacrylic acid methyl and ethyl esters with a low content in quaternary ammonium groups. Glycerin is dissolved in 100 mL of 95% ethanol. These solutions are blended.

Semipermeable Membrane of Comparative Example B

The semipermeable membrane of Comparative Example B is prepared in the same manner as the semipermeable membrane of Examples 1 to 4, except that no EUDRAGIT™ RL 100 is used.

Tablets Preparation

The ingredients of the drug layer are pressed to a first layer and then the ingredients of the push layer are compressed and subsequently pressed on the drug layer. 170 mL the coating formulation solution are sprayed at 2.15 mL/min on to the rotating tablets in the coating pan. The coating conditions are kept at 45-60% relative humidity. After the coating process is completed, a hole is drilled by laser through the semi-permeable membrane. The diameter of the hole should be less than 2 mm Comparative Example A Comparative Example A is a commercially available osmotic dosage form wherein the semi-permeable membrane consists of cellulose acetate and polyethylene glycol.

TABLE 2

| Formulation for Osmotic Dosage Form | Example 1 | Example 2 | Example 3 | Example 4 | Comparative Example B |
|---|---|---|---|---|---|
| Drug Layer | | | | | |
| Glipizide | 11 mg | 11 mg | 11 mg | 11 mg | 11 mg |
| POLYOX ™ WSR N-80 | 80 mg | 80 mg | 80 mg | 80 mg | 80 mg |
| $Fe_2O_3$ | 0.05 mg | 0.05 mg | 0.05 mg | 0.05 mg | 0.05 mg |
| Magnesium stearate | 0.5 mg | 0.5 mg | 0.5 mg | 0.5 mg | 0.5 mg |
| Push Layer | | | | | |
| POLYOX WSR Coagulant | 20 mg | 20 mg | 20 mg | 20 mg | 20 mg |
| POLYOX WSR N750 | 13.5 mg | 13.5 mg | 13.5 mg | 13.5 mg | 13.5 mg |
| METHOCEL E5 | 5 mg | 5 mg | 5 mg | 5 mg | 5 mg |
| NaCl | 30 mg | 30 mg | 30 mg | 30 mg | 30 mg |
| $Fe_3O_4$ | 1 mg | 1 mg | 1 mg | 1 mg | 1 mg |
| Magnesium stearate | 0.5 mg | 0.5 mg | 0.5 mg | 0.5 mg | 0.5 mg |
| Semipermeable Membrane (for 1000 tablets) | | | | | |
| ETHOCEL Standard 20 Premium | 30 g | 30 g | 30 g | 30 g | 30 g |
| Eudragit RL100 | 7.5 g | 7.5 g | 7.5 g | 7.5 g | |
| Glycerin | 13.125 g | 13.125 g | 12 g | 12 g | 13.5 g |
| Weight of semipermeable membrane (weight gain per tablet) | 12.89 mg | 11.3 mg | 12 mg | 9 mg | 14 mg |

The drug release is tested by placing 6 samples of the osmotic dosage form in a buffer solution which is prepared by dissolving 54.4 g $KH_2PO_4$ and 7.168 g NaOH into 8 L water to produce a solution with a pH of 6.8. The temperature of the buffer solution is kept at 37° C. by means of a water bath. The drug release is measured at 0 hours, 2 hours, 4 hours, 8 hours, 12 hours and 16 hours by UV-spectrophotometric method at 276 nm and a path length (cuvette thickness) of 1 cm. The concentration of the drug in the artificial intestinal juice is determined by comparing the UV absorption with the UV absorption of a series of standard solutions of glipizide in methanol at concentrations of 1, 2, 4, 8, 10, 12 and 20 microgram/ml.

The drug release test is repeated three times to test the reproducibility. The results are listed in Table 3.

TABLE 3

| Average Release of 6 tablets (%) | Example 1 Test 1 | Example 1 Test 2 | Example 1 Test 3 | Comparative Example A |
|---|---|---|---|---|
| 0 | 2% | 0% | 1% | 0 |
| 2 | 4% | 3% | 3% | 0.4% |
| 4 | 22% | 23% | 24% | 21% |
| 8 | 55% | 54% | 63% | 60% |
| 12 | 90% | 88% | 91% | 93% |
| 16 | 103% | 96% | 101% | 103% |

The results of Table 3 illustrate that the osmotic dosage form of the present invention can be tailor-made to achieve essentially the same drug release profile as Comparative Example A, which comprises cellulose acetate as the film-forming polymer in the semi-permeable membrane. The drug release profile of Example 1 meets the requirement for zero order release from 2-12 hour. After linear fitting, $R^2$ for Example 1, Test 1 is 0.999; Example 1, Test 2 is 0.9986 and Example 1, Test 3 is 0.9924 and for Comparative Example A is 0.9878.

TABLE 4

| Average Release of 6 tablets (%) | Example 2 | Example 3 | Example 4 | Comparative Example A | Comparative Example B |
|---|---|---|---|---|---|
| 0 | 2% | 1% | 12% | 0 | 0 |
| 2 | 14% | 2% | 12% | 0.4% | 1.3% |
| 4 | 36% | 16% | 25% | 21% | 14.4% |
| 8 | 76% | 40% | 51% | 60% | 45.6% |
| 12 | 96% | 63% | 76% | 93% | 74.2% |
| 16 | 97% | 84% | 94% | 103% | 89.2% |

The osmotic dosage form of Example 4 achieves an equivalent drug release profile as Comparative Example A at 4-16 hours, and even does not have a significant lag-time between the intake of the osmotic dosage form and the onset of the release biologically active ingredient as the osmotic dosage form of Comparative Example A.

The drug release profiles of Examples 2-4 meet the requirement for zero order release from 2-12 hour. After linear fitting, $R^2$ for Example 2 is 0.9736; Example 3 is 0.9988, Example 4 is 0.9999 and for Comparative Example A is 0.9878. After linear fitting, $R^2$ for Comparative Example B is 0.98.

In Comparative Example B all tablets are found to be broken when the osmotic dosage form is contacted with the buffer solution. This is unacceptable for an osmotic dosage form.

List of Reference Numerals
101 osmotic dosage form
102 core
105 semi-permeable membrane
106 passageway
201 osmotic dosage form
202 core
203 push layer
204 biologically active ingredient
205 semi-permeable membrane
206 passageway
207 drug layer
301 osmotic dosage form
302 core 303 push layer
305 semi-permeable membrane
306 passageway
307 drug layer

The invention claimed is:

1. An osmotic dosage form comprising:
   (a) a core comprising
      (i) a drug layer comprising, based on the total weight of the drug layer, from 4 to 50 weight percent of the biologically active ingredient, and
      (ii) a push layer comprising, based on the total weight of the push layer, from 15 to 60 weight percent of one or more ethylene oxide polymers, from 1 to 10 weight percent of one or more binding agents selected from the group consisting of methyl cellulose, hydroxypropyl cellulose, hydroxyethyl cellulose, hydroxypropyl methylcellulose, carboxymethyl cellulose, and polyvinyl pyrrolidone, and from 15 to 50 weight percent of one or more osmotic agents;
   (b) a semi-permeable membrane covering said core, comprising
      (i) from 30 to 70 weight percent of ethyl cellulose,
      (ii) from 5 to 40 weight percent of a homopolymer or copolymer of an acrylic or methacrylic acid ester and
      (iii) from 10 to 40 weight percent of a water-soluble plasticizer selected from the group consisting of triethyl citrate, triacetin, and glycerol, with the provisos that (1) the semi-permeable membrane comprises no or not more than 5 weight percent of a water-soluble material excluding any water-soluble plasticizer and (2) the semi-permeable membrane does not comprise cellulose acetate as the film-forming material and (3) components (i), (ii) and (iii) make up from 85 to 100 percent of the film-forming membrane, based on the total dry weight of the semi-permeable membrane, wherein the semi-permeable membrane maintains its physical and chemical integrity during the time the biologically active ingredient is released; and
   (c) at least one drilled osmotic passageway through the semi-permeable membrane to the core, wherein the dosage form provides controlled release of the biologically active agent.

2. The osmotic dosage form of claim 1, wherein the weight ratio between the ethyl cellulose and the homopolymer or copolymer of an acrylic or methacrylic acid ester in the semi-permeable membrane is from 0.1 to 15:1.

3. The osmotic dosage form of claim 1, wherein the total weight of ethyl cellulose, the homopolymer or copolymer of an acrylic or methacrylic acid ester, and the water-soluble plasticizer is from 95 to 100 percent, based on the total dry weight of the semi-permeable membrane.

4. The osmotic dosage form of claim 1, wherein the drug layer in the core further comprises from 15 to 90 weight percent of one or more ethylene oxide polymers.

5. The osmotic dosage form of claim 1, wherein the accumulated drug release in percent between 2 and 12 hours meets the formula for zero order release when t is between 2 and 12 hours:

$Y=100k(t-Tlag)$ after fitting test, wherein Tlag is a lagging time of 2 hours, Y is the accumulated drug release in percent and k is a constant, and after linear fitting the correlation coefficient $R^2$ is >0.9.

6. The osmotic dosage form of claim 1, characterized by not having a lag-time between the intake of the osmotic dosage form and the onset of the release biologically active ingredient.

* * * * *